(12) United States Patent
Usui et al.

(10) Patent No.: US 8,073,539 B2
(45) Date of Patent: Dec. 6, 2011

(54) HEART TREATMENT DEVICE

(75) Inventors: Takeo Usui, Tokyo (JP); Kazuhito Nemoto, Tokyo (JP)

(73) Assignee: Olympus Corporation, Tokyo (JP)

(*) Notice: Subject to any disclaimer, the term of this patent is extended or adjusted under 35 U.S.C. 154(b) by 43 days.

(21) Appl. No.: 12/818,715

(22) Filed: Jun. 18, 2010

(65) Prior Publication Data

US 2010/0331907 A1    Dec. 30, 2010

(30) Foreign Application Priority Data

Jun. 26, 2009   (JP) .................... 2009-152067
Sep. 3, 2009    (JP) .................... 2009-203556

(51) Int. Cl.
*A61N 1/00*   (2006.01)
(52) U.S. Cl. ........................................... 607/17
(58) Field of Classification Search .............. 607/17
See application file for complete search history.

(56) References Cited

U.S. PATENT DOCUMENTS
7,191,012 B2 * 3/2007 Boveja et al. ............... 607/60

FOREIGN PATENT DOCUMENTS
| JP | 8-38625 | 2/1996 |
| JP | 2004-173790 | 6/2004 |
| JP | 2009-028397 | 2/2009 |

* cited by examiner

*Primary Examiner* — George Manuel
(74) *Attorney, Agent, or Firm* — Scully, Scott, Murphy & Presser, P.C.

(57) ABSTRACT

Provided is a heart treatment device (1) including a heartbeat detecting unit (2) that detects heartbeats by using an electrode disposed at a heart (A), a pulse transformer (5) having a primary winding (5a) and a secondary winding (5b), the heartbeat detecting unit (2) being disposed on the side of the primary winding (5a) and the secondary winding (5b) being connected to the vagus nerve (B), and a pulse generating unit (8) that supplies an electric pulse to the primary winding (5a) of the pulse transformer (5) on the basis of the heartbeats detected by the heartbeat detecting unit (2), the electric pulse having a pulse width not exceeding the voltage-time product of the pulse transformer (5).

6 Claims, 11 Drawing Sheets

HEART TREATMENT DEVICE

BACKGROUND OF THE INVENTION

1. Field of the Invention

The present invention relates to heart treatment devices.

This application is based on Japanese Patent Applications Nos. 2009-152067 and 2009-203556, the contents of which are incorporated herein by reference.

2. Description of Related Art

Conventionally known heart treatment devices treat fibrillation or tachycardia of the heart by electrically stimulating the vagus nerve when fibrillation or tachycardia occurs (e.g., Japanese Unexamined Patent Applications, Publications Nos. Hei 8-38625, 2004-173790, and 2009-28397).

In Japanese Unexamined Patent Application, Publication No. Hei 8-38625, electric pulses having a pulse width of one tenth to several tenths of milliseconds are used to stimulate the vagus nerve. In Japanese Unexamined Patent Application, Publication No. 2009-28397, a vagus-nerve stimulating unit that outputs electric pulses to the vagus nerve is electrically insulated from a heartbeat detecting unit, thereby preventing leakage of the electric pulses to the heartbeat detecting unit. Furthermore, electric power supplies are provided individually in mutually insulated regions.

BRIEF SUMMARY OF THE INVENTION

The present invention provides a heart treatment device including a heartbeat detecting unit that detects heartbeats by using an electrode disposed at a heart; a pulse transformer having a primary winding and a secondary winding, the heartbeat detecting unit being disposed on the side of the primary winding, and the secondary winding being connected to the vagus nerve; and a pulse generating unit that supplies an electric pulse to the primary winding of the pulse transformer on the basis of the heartbeats detected by the heartbeat detecting unit, the electric pulse having a pulse width not exceeding the voltage-time (VT) product of the pulse transformer.

DETAILED DESCRIPTION OF THE INVENTION

A heart treatment device 1 according to a first embodiment of the present invention will be described below with reference to FIGS. 1 to 7.

Figure 1:
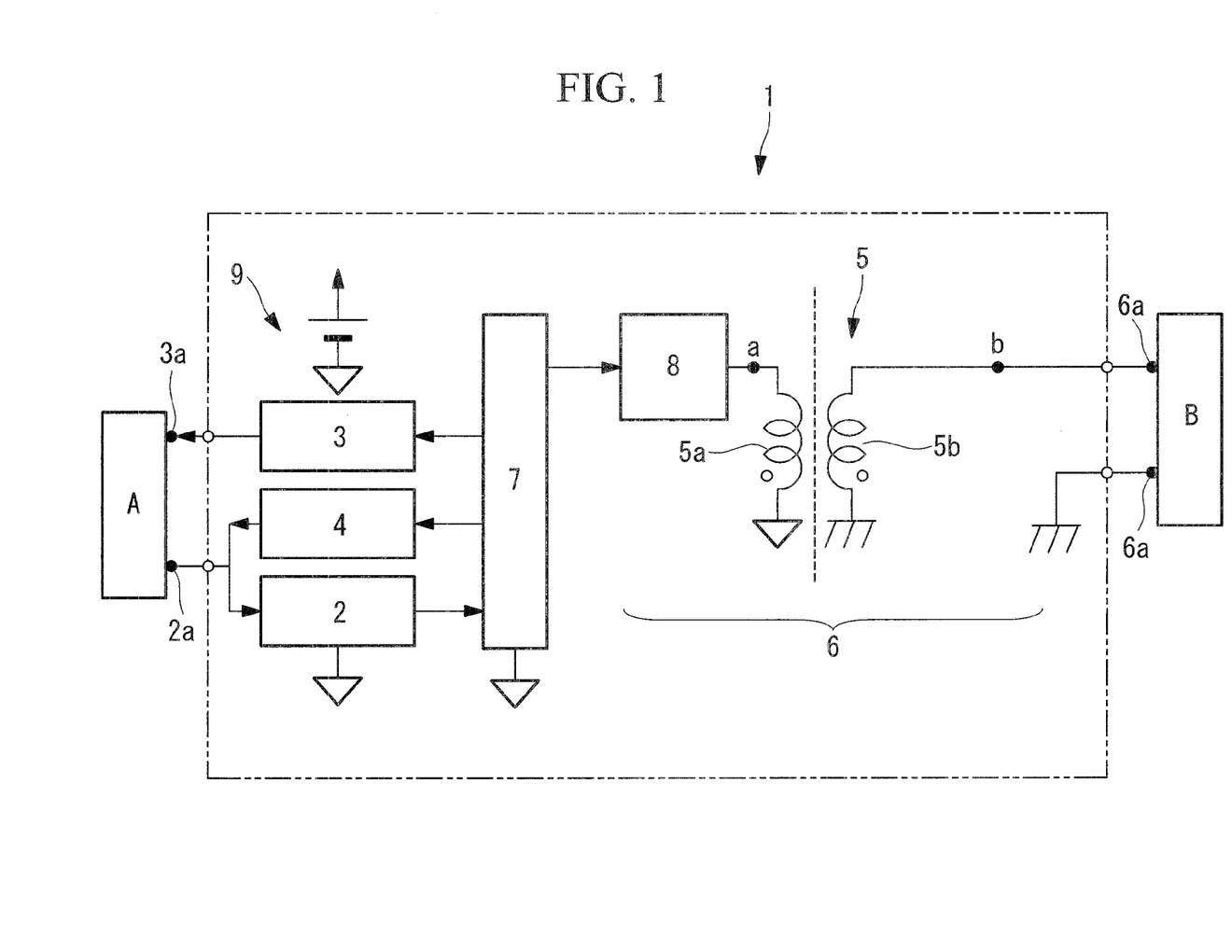
FIG. 1 is an overall configuration diagram of a heart treatment device according to a first embodiment of the present invention.

As shown in FIG. 1, the heart treatment device 1 according to this embodiment includes a heartbeat detecting circuit (heartbeat detecting unit) 2 that detects heartbeats, a defibrillation-pulse generating unit 3 and a pacing-pulse generating unit 4 that supply defibrillation pulses and pacing pulses to the heart A, respectively, a vagus-nerve stimulating unit 6 having a pulse transformer 5 connected to the vagus nerve B, and a control unit 7 that controls the defibrillation-pulse generating unit 3, the pacing-pulse generating unit 4, and the vagus-nerve stimulating unit 6.

The heartbeat detecting circuit 2 detects heartbeats based on the waveform of electrocardiograph signals acquired on the basis of a change in potential at a sensing/pacing electrode 2a disposed at the heart A.

Similarly to the configuration of existing heart treatment devices, the defibrillation-pulse generating unit 3 and the pacing-pulse generating unit 4 are configured to generate defibrillation pulses or pacing pulses by instantaneously releasing charges from a charged capacitor (not shown) to the heart A. Upon occurrence of fibrillation, the defibrillation-pulse generating unit 3 supplies defibrillation pulses for defibrillation, having a relatively large energy, to the heart A via a defibrillation electrode 3a connected to the heart A. On the other hand, upon occurrence of bradycardia, the pacing-pulse generating unit 4 supplies pacing pulses to the heart A via the sensing/pacing electrode 2a shared with the heartbeat detecting circuit 2. The pacing pulses have a smaller energy compared with the defibrillation pulses and are supplied successively at time intervals shorter than the time intervals corresponding to the heart rate in normal conditions.

The vagus-nerve stimulating unit 6 includes a digital-to-analog (DA) converter (pulse generator) 8 and the pulse transformer 5. The DA converter 8 receives an input digital signal from the control unit 7. The pulse transformer 5 has primary winding 5a connected to the DA converter 8 and secondary winding 5b connected to the vagus nerve B via a nerve electrode 6a. Upon input of a digital signal from the control unit 7 to the DA converter 8, the DA converter 8 converts the digital signal into a rectangular-wave analog signal, i.e., a stimulation pulse (electric pulse), which is input to the primary winding 5a. Thus, it is possible to supply the stimulation pulse to the vagus nerve B connected to the secondary winding 5b, thereby stimulating the vagus nerve B. At this time, the DA converter 8 outputs a stimulation pulse having a voltage substantially the same as the voltage of a battery 9 provided in the heart treatment device 1.

Generally, the size of the pulse transformer 5 increases as the VT product thereof becomes greater. Thus, as the pulse transformer 5, a pulse transformer having outer dimensions sufficiently small for embedding in a living body, i.e., a pulse transformer having a relatively small VT product, is chosen. Furthermore, as the pulse transformer 5, a pulse transformer having a suitable winding ratio between the primary winding 5a and the secondary winding 5b thereof in accordance with the voltage of the battery 9 provided on the side of the primary winding 5a and the voltage of a stimulation pulse to be supplied to the vagus nerve B is chosen.

For example, suppose here that, the battery 9 used has a voltage of 3 V and the pulse transformer 5 used has a VT product of 3 V·μs, as is generally the case with embedded heart treatment devices. In this case, assuming that the voltage of the stimulation pulse supplied to the primary winding 5a is 3 V, the upper limit of the pulse width is about 1 μs. Furthermore, suppose here that the pulse transformer 5 used has a 1:3 winding ratio between the primary winding 5a and the secondary winding 5b. Thus, the voltage of the stimulation pulse at point b in FIG. 1 is boosted to three times the voltage of the stimulation pulse at point a in FIG. 1, i.e., to 9 V, as indicated by solid lines in FIGS. 2A and 2B.

The control unit 7 monitors the time interval T of heartbeats sequentially detected by the heartbeat detecting circuit 2. Then, the control unit 7 detects tachycardia when the time interval T of heartbeats is less than a first predetermined lower limit T1, detects fibrillation when the time interval T is less than a second predetermined lower limit T2, which is even lower than the first predetermined lower limit T1, and detects bradycardia when the time interval T is greater than a predetermined upper limit T3. Upon detecting one of these abnormalities, on the basis of the detection result, the control unit 7 causes the defibrillation-pulse generating unit 3 or the pacing-pulse generating unit 4 to output defibrillation pulses or pacing pulses or outputs a digital signal to the DA converter 8.

The operation of the thus-configured heart treatment device 1 will be described below with reference to FIG. 3.

In the heart treatment device 1 according to this embodiment, upon commencing detection of heartbeats (step S1), the time interval T of the heartbeats is monitored constantly (step S2). When fibrillation of the heart A occurs and the time interval T of the heartbeats becomes less than the second predetermined lower limit T2 (step S3), defibrillation pulses are supplied to the heart A (step S4) to perform defibrillation. When tachycardia of the heart A occurs and the time interval T of the heartbeats becomes less than the first predetermined lower limit T1 (step S5), a stimulation pulse is output to the vagus nerve B (step S6) to reduce the heart rate to within the normal range. When bradycardia of the heart A occurs and the time interval T of the heartbeats exceeds the predetermined upper limit T3 (step S7), pacing pulses are output to the heart A (step S8) to raise the heart rate to within the normal range.

In this case, according to this embodiment, with the heartbeat detecting circuit 2 and the vagus nerve B disposed on the sides of the different windings 5a and 5b of the pulse transformer 5 and electrically insulated from each other, a stimulation pulse generated on the side of the primary winding 5a of the pulse transformer 5 is conveyed to the vagus nerve B. Thus, leakage of the stimulation pulse to the heartbeat detecting circuit 2 is prevented. Accordingly, an advantage is afforded in that it is possible to detect heartbeats accurately even when the vagus nerve B is being stimulated. Furthermore, since a single electric power supply suffices, an advantage is afforded in that reduction of power consumption and size reduction of the heart treatment device 1 can be achieved. Furthermore, the stimulation pulse generated on the side of the primary winding 5a is boosted by the pulse transformer 5 from the voltage of the battery 9 to a voltage suitable for stimulating the vagus nerve B. Thus, a component for boosting the stimulation pulse generated by the DA converter 8, such as a boosting circuit, becomes unnecessary. Accordingly, an advantage is afforded in that further reduction in power consumption and further size reduction of the heart treatment device 1 can be achieved. Furthermore, by using a stimulation pulse having a sufficiently smaller pulse width compared with the pulse width of an electric pulse used for stimulating the vagus nerve B in existing devices, an advantage is afforded in that unintended effects on the vagus nerve B and excessive stimulation of the vagus nerve B can be prevented.

In the embodiment described above, stimulation pulses may be supplied to the vagus nerve B in a burst-like manner.

Figure 2A:
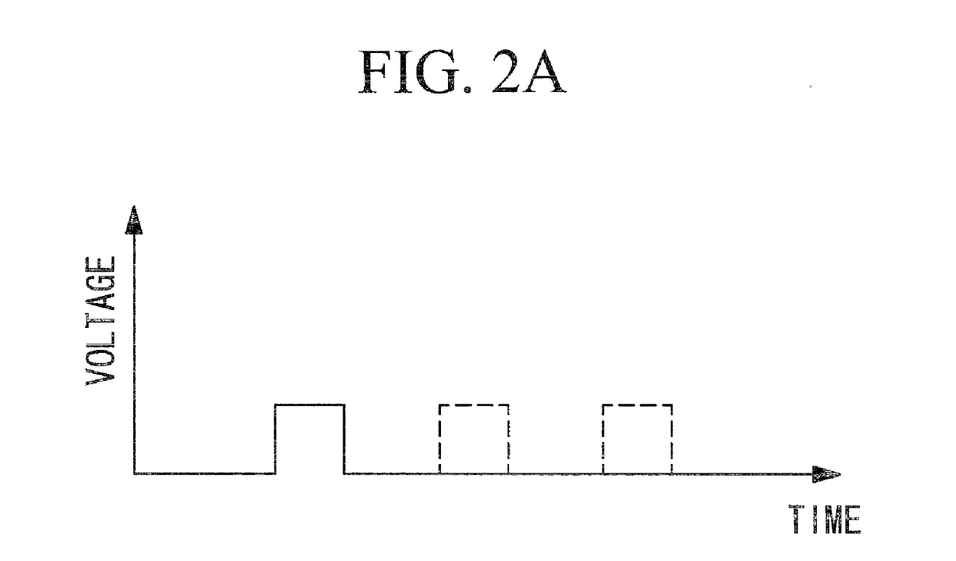
FIGS. 2A and 2B are graphs showing stimulation pulses at points a and b in FIG. 1, respectively.
Figure 2B:
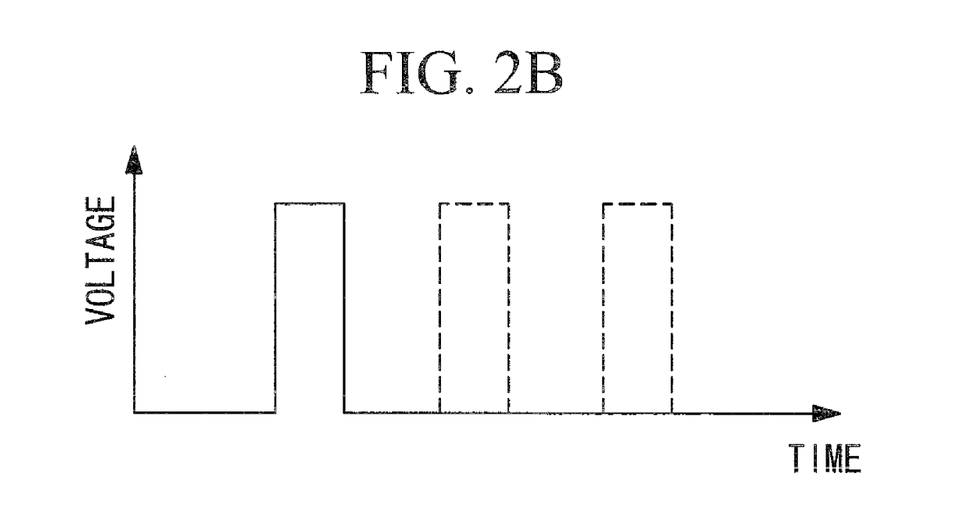

For example, as indicated by chain lines in FIGS. 2A and 2B, a stimulation pulse is output a number of times such that the stimulation pulses are separated by time intervals substantially as long as the pulse width of the individual stimulation pulses. Accordingly, it is possible to stimulate the vagus nerve B more strongly, thereby stopping tachycardia more effectively.

Furthermore, although stimulation pulses are supplied to the vagus nerve B by using the single pulse transformer 5 in the embodiment described above, alternatively, stimulation pulses may be supplied successively to the vagus nerve B by using a plurality of pulse transformers 5.

When the pulse transformer 5 used is small, the VT product thereof is relatively small. Thus, the pulse width of stimulation pulses that can be supplied simultaneously by a single pulse transformer 5 is limited to a relatively small width. With a design based on the configuration of existing heart treatment devices, as in the example described above, the pulse width that can actually be achieved in the heart treatment device 1 according to this embodiment is about 1 μs.

Figure 4:
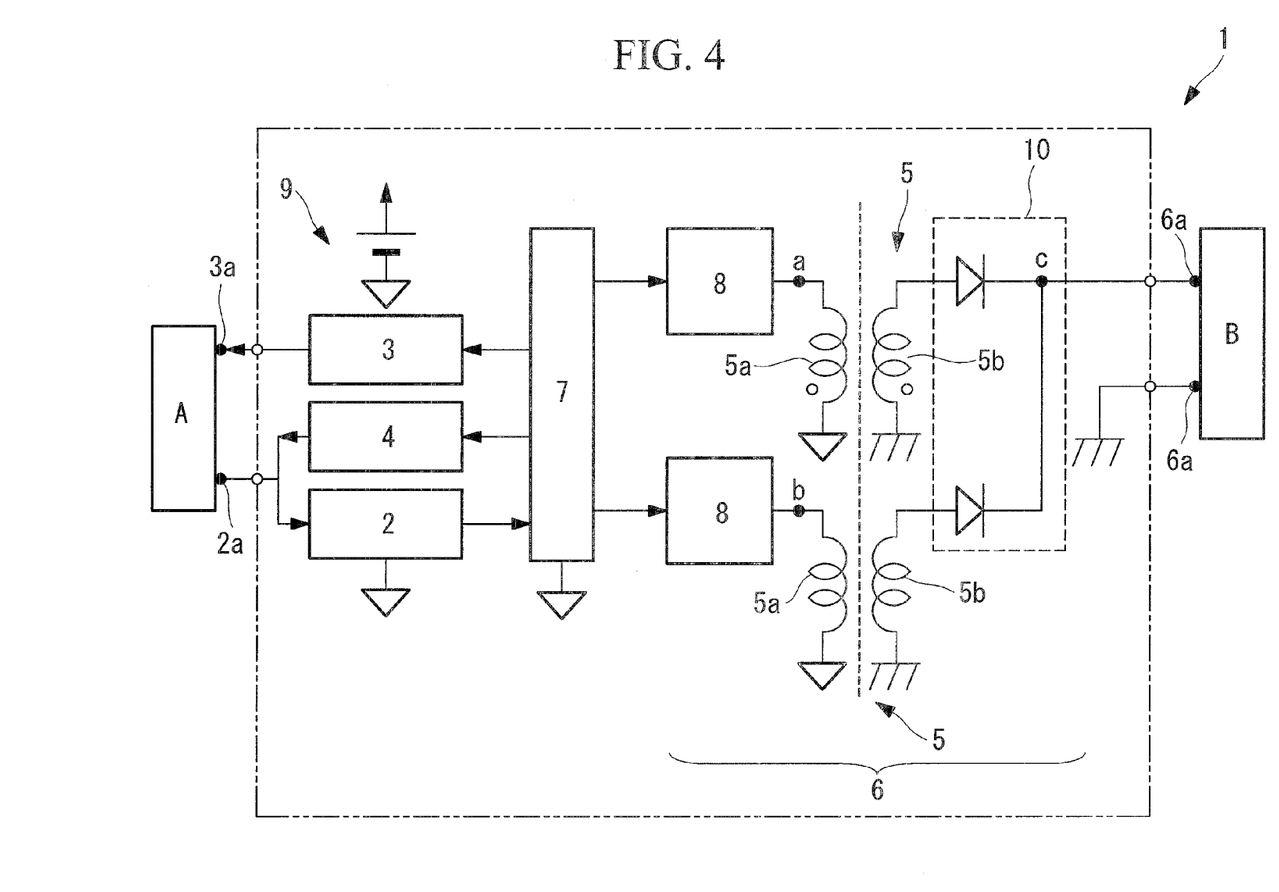
FIG. 4 is a diagram showing a modification of the heart treatment device shown in FIG. 1.
Figure 5A:
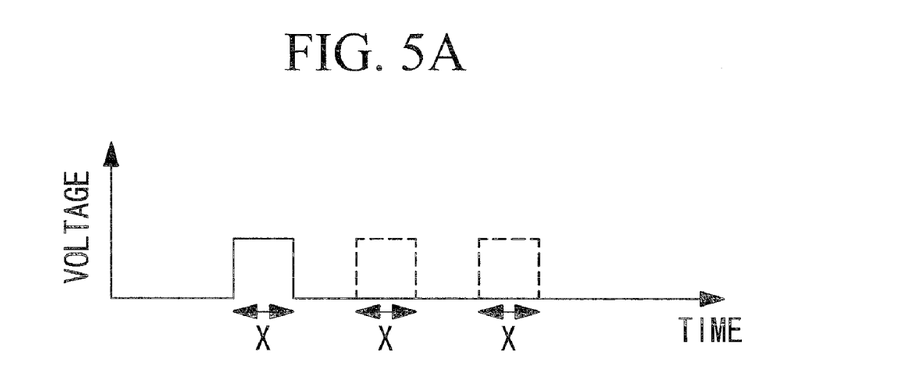
FIGS. 5A, 5B, and 5C are graphs showing stimulation pulses at points a, b, and c in FIG. 4, respectively.
Figure 5B:
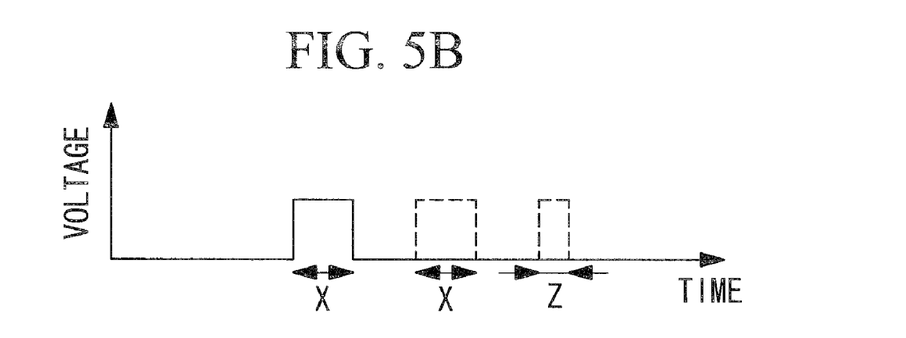
Figure 5C:
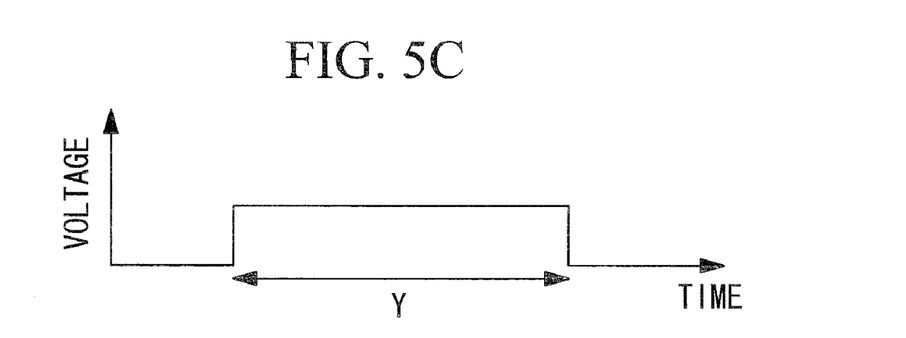

For example, when two DA converters 8 and two pulse transformers 5 are used, as shown in FIG. 4, the control unit (transformer selecting means) 7 inputs successively output digital signals alternately to the DA converters 8. Thus, as shown in FIGS. 5A and 5B, stimulation pulses are generated alternately at points a and b in FIG. 4. As shown in FIG. 5C, at point c in FIG. 4, these stimulation pulses can be regarded as a single stimulation pulse with an extended pulse width. That is, a stimulation pulse having an extended pulse width and increased energy is supplied to the vagus nerve B.

In this case, in order to prevent an unintended pulse transformer 5 from acting as a load of stimulation pulses output from the DA converters 8, rectifying circuits 10, such as diodes, are provided downstream of the individual pulse transformers 5. The rectifying circuit 10 can also serve to prevent stimulation pulses supplied from one of the pulse transformers 5 to the vagus nerve B from flowing backward into the other pulse transformer 5 via the vagus nerve B.

Figure 6:
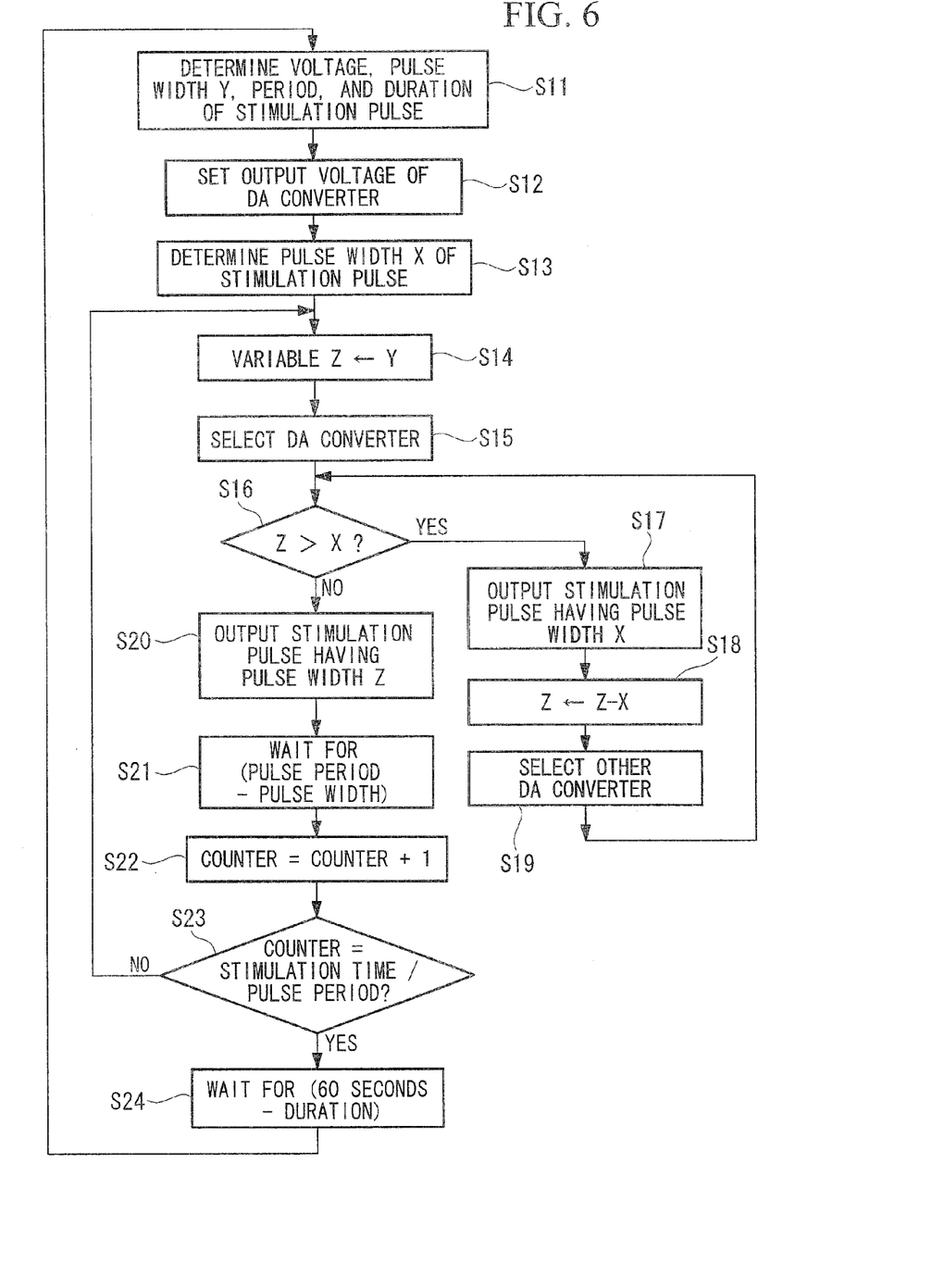
FIG. 6 is a flowchart for explaining the operation of a vagus-nerve stimulating unit of the heart treatment device shown in FIG. 4.

The operation of the thus-configured vagus-nerve stimulating unit 6 and control unit 7 will be described below with reference to FIG. 6. In the description, a pulse width X denotes the pulse width of each stimulation pulse, and a pulse width Y denotes the pulse width of a series of stimulation pulses as a whole that is to be supplied to the vagus nerve B.

When tachycardia is detected by the control unit 7, in accordance with the specification of stimulation pulses determined by the control unit 7 (step S11), the control unit 7 sets an output voltage of the DA converter 8 (step S12) and determines the pulse width X of stimulation pulses (step S13), which is restricted by the output voltage and the VT product of the pulse transformers 5. Then, the control unit 7 sets the pulse width Y to a variable Z representing the sum of the pulse widths of stimulation pulses that have been supplied to the vagus nerve B (step S14) and selects one of the DA converters 8 (step S15).

If the variable Z is greater than the pulse width X (step S16), the control unit 7 outputs a stimulation pulse having the pulse width X (step S17) and subtracts the pulse width X of the output stimulation pulse from the variable Z (step S18). In this manner, while alternately switching to the other DA converter 8 (step S19), the control unit 7 repeats outputting a stimulation pulse having the pulse width X. When the variable Z has become less than the pulse width X (step S16), the control unit 7 outputs a stimulation pulse having the pulse width Z (step S20). Thus, a stimulation pulse having a pulse width Y as a whole is supplied to the vagus nerve B.

In this manner, at a predetermined time cycle (step S21), while incrementing a counter (step S22), the vagus-nerve stimulating unit 6 and the control unit 7 repeat supplying a stimulation pulse having a pulse width Y to the vagus nerve B a predetermined number of times (step S23). When stimulation over a set duration is finished, the control unit 7 monitors the heartbeats during a certain period, for example, during a period obtained by subtracting the duration from 60 seconds (step S24), to determine whether tachycardia has been stopped.

Thus, even if the energy of each stimulation pulse output from the pulse transformers 5 is not sufficient for stimulating the vagus nerve B, it is possible to increase the energy of the stimulation pulse appropriately.

Furthermore, since it is possible to further decrease the energy of each pulse, it is possible to reduce the VT product of the pulse transformers 5 to reduce the size thereof, which contributes to size reduction of the heart treatment device 1. Furthermore, by further decreasing the energy of each stimulation pulse, it is possible to adjust the energy of the stimulation pulse supplied to the vagus nerve B as a whole with a smaller pulse width, thereby stimulating the vagus nerve B with a more appropriate strength.

In this case, stimulation pulses may be supplied to the individual pulse transformers 5 from a single DA converter 8 by alternately switching the path with a switch or the like. Accordingly, it is possible to further simplify the configuration of the heart treatment device 1 and further reduce its size.

Furthermore, in the case where a plurality of pulse transformers 5 are used, the voltages of stimulation pulses input to the individual pulse transformers 5 may be varied.

Figure 7A:
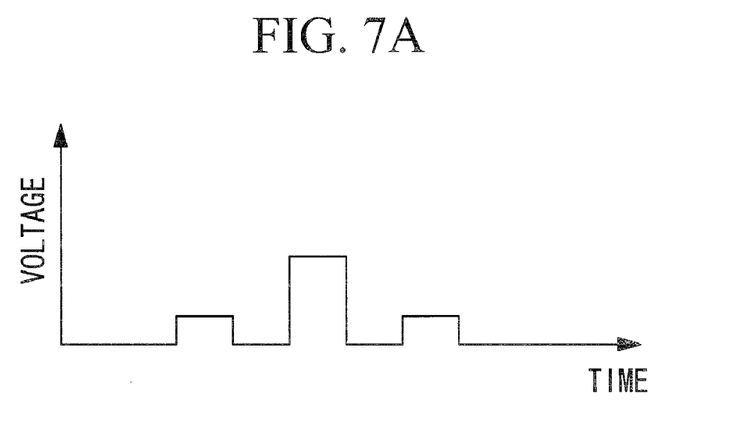
FIGS. 7A, 7B, and 7C are graphs showing a modification of stimulation pulses at points a, b, and c in FIG. 4, respectively.
Figure 7B:
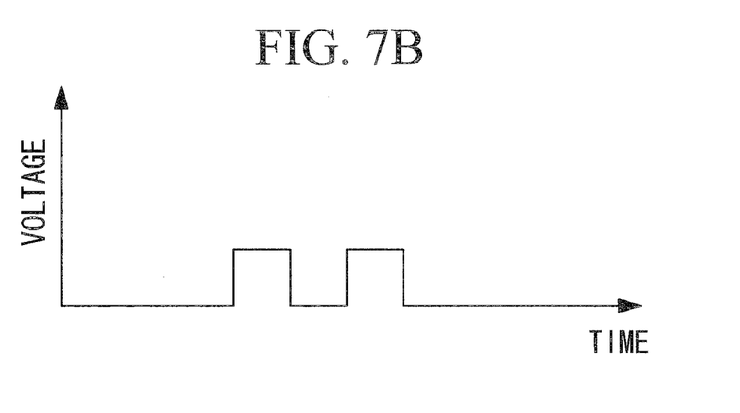
Figure 7C:
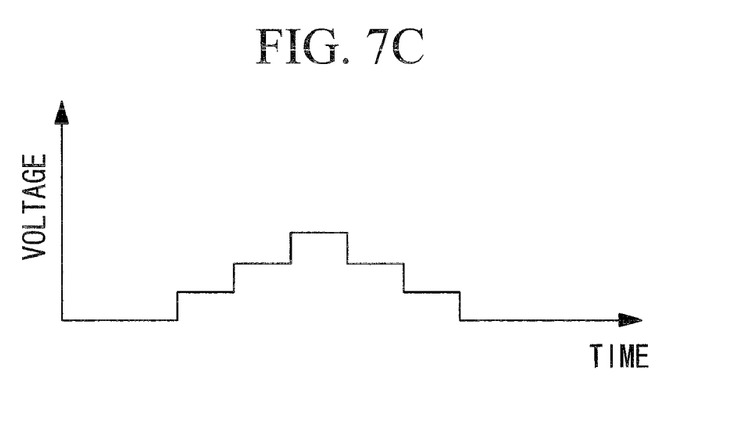

For example, as shown in FIGS. 7A and 7B, when stimulation pulses are input alternately to the individual pulse transformers 5 while boosting and reducing the voltage, the stimulation pulse as a whole is shaped approximately into a triangular wave, as shown in FIG. 7C. Thus, it becomes possible to shape the stimulation pulse supplied to the vagus nerve B into various shapes not limited to a rectangular wave. Accordingly, by using a stimulation pulse having a suitable shape in accordance with the treatment, it is possible to improve the effectiveness of the treatment with the heart treatment device 1.

Next, a heart treatment device 1 according to a second embodiment of the present invention will be described below with reference to FIGS. 8 to 11. Parts that are common to those in the first embodiment described above are designated by the same numerals, and descriptions thereof will be omitted.

Figure 8:
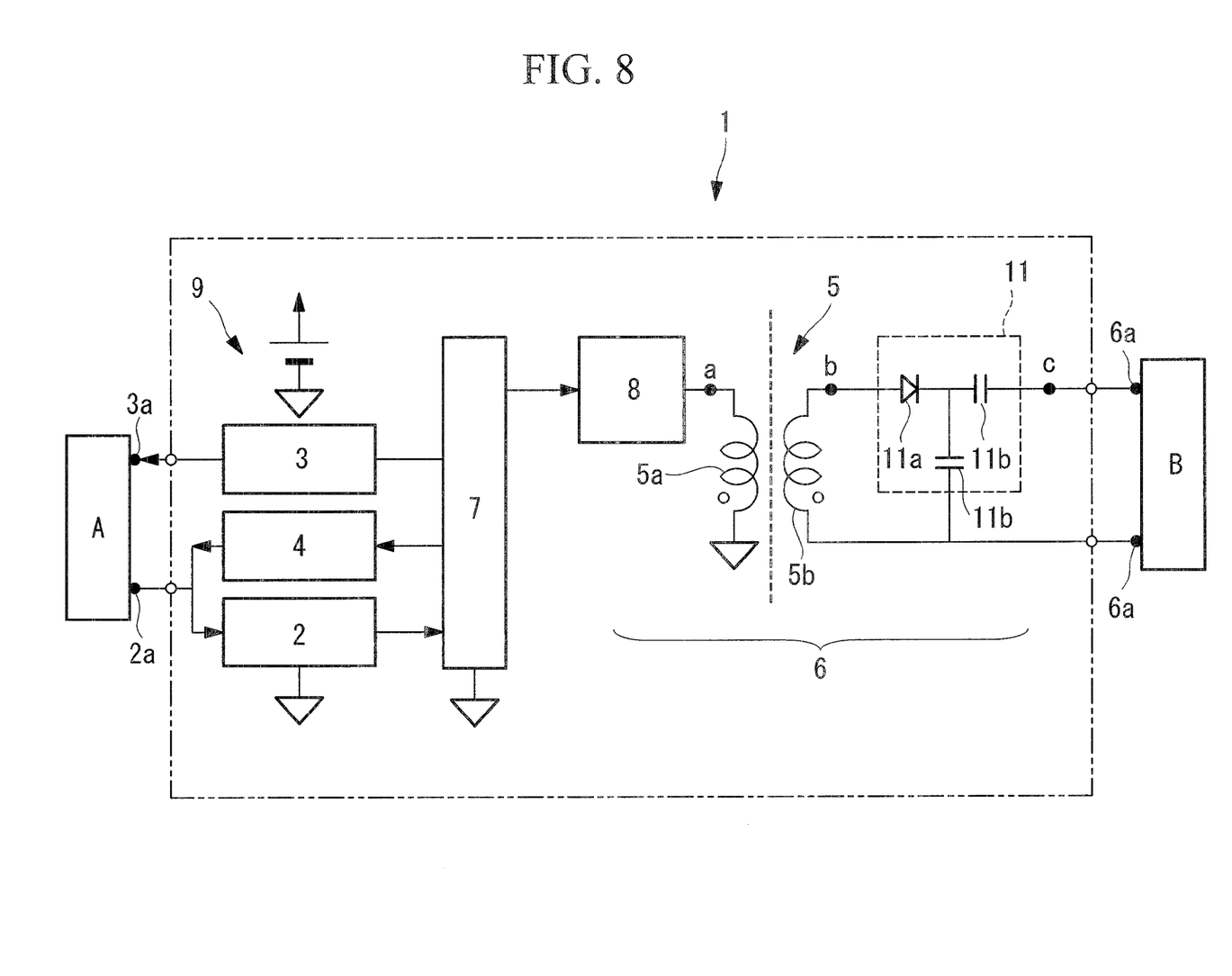
FIG. 8 is an overall configuration diagram of a heart treatment device according to a second embodiment of the present invention.

As shown in FIG. 8, the heart treatment device 1 according to this embodiment differs from the heart treatment device 1 according to the first embodiment in that the vagus-nerve stimulating unit 6 includes a pulse transformer 5 and a smoothing circuit (smoothing means) 11.

The secondary winding 5b of the pulse transformer 5 in the vagus-nerve stimulating unit 6 is connected to the nerve electrode 6a via the smoothing circuit 11. For example, the smoothing circuit 11 includes a rectifying element 11a, such as a diode, and a capacitor 11b.

Figure 9A:
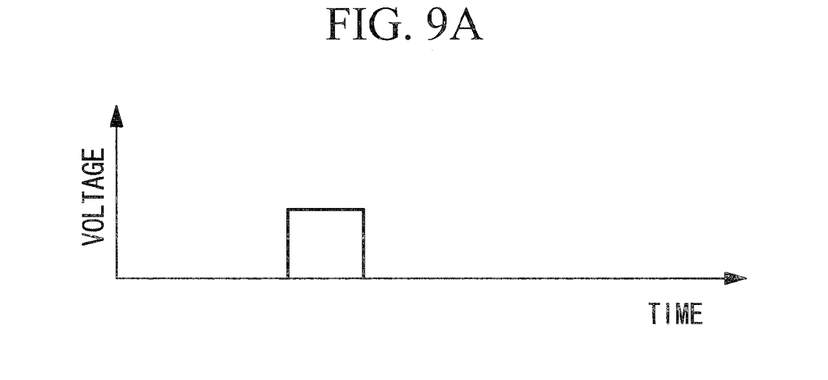
FIGS. 9A, 9B, and 9C are graphs showing the shapes of stimulation pulses at points a, b, and c in a case where a single stimulation pulse is generated in the heart treatment device shown in FIG. 8.
Figure 9B:
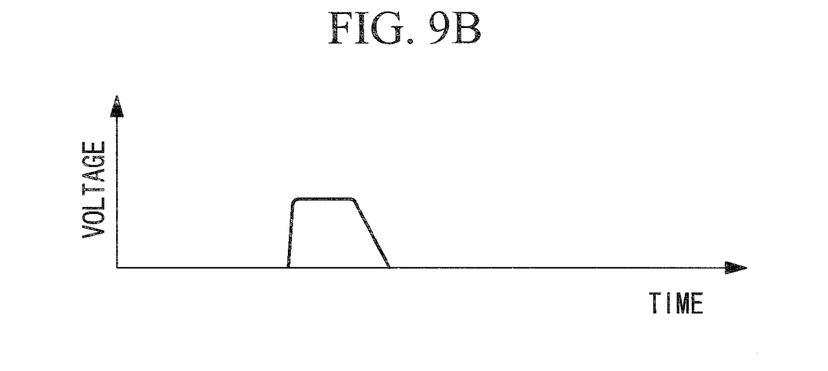
Figure 9C:
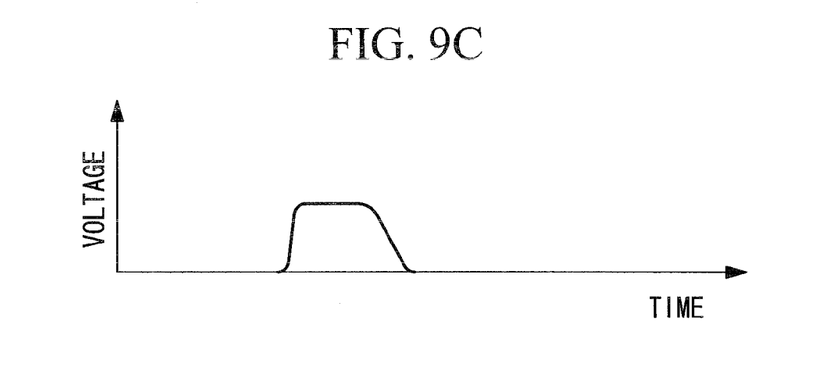

The DA converter 8 converts a digital signal input from the control unit 7 into a rectangular-wave analog signal, i.e., a stimulation pulse (electric pulse), and outputs the stimulation pulse, as shown in FIG. 9A. The output stimulation pulse is conveyed from the primary winding 5a to the secondary winding 5b of the pulse transformer 5. At this time, the waveform becomes distorted, as shown in FIG. 9B. The stimulation pulse then passes through the smoothing circuit 11. At this time, the voltage is smoothed so that the rising and falling of the waveform become less steep. As a result, a smoothed stimulation pulse is supplied to the vagus nerve B via the nerve electrode 6a.

Figure 10A:
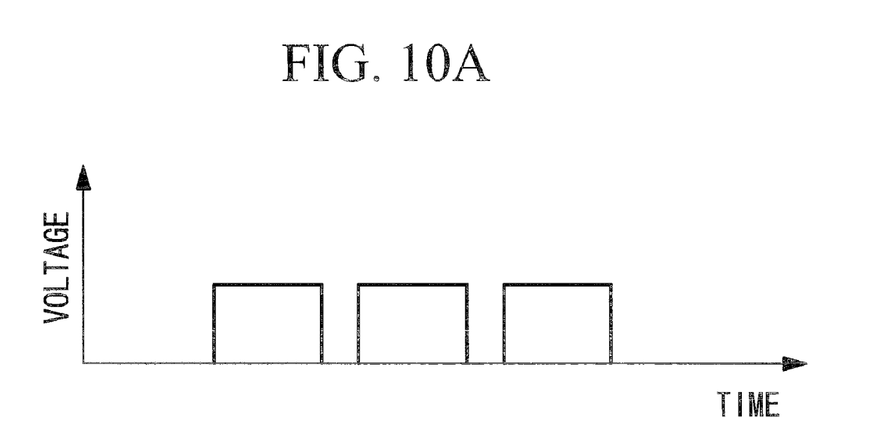
FIGS. 10A, 10B, and 10C are graphs showing the shape of stimulation pulses at points a, b, and c in a case where successive stimulation pulses are generated in the heart treatment device shown in FIG. 8.
Figure 10B:
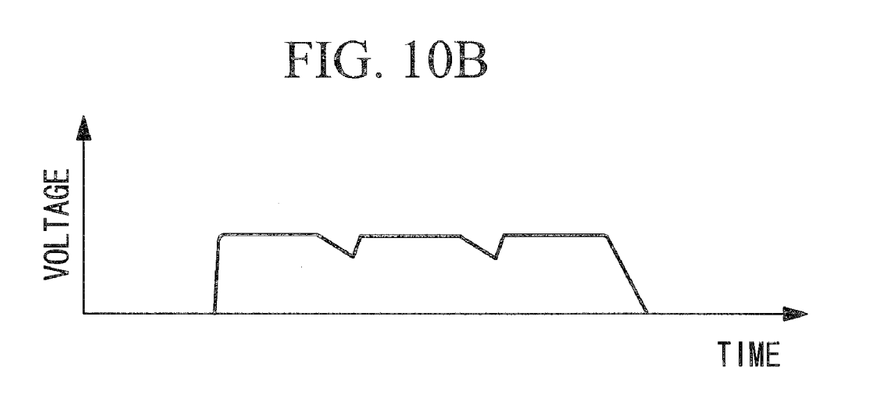
Figure 10C:
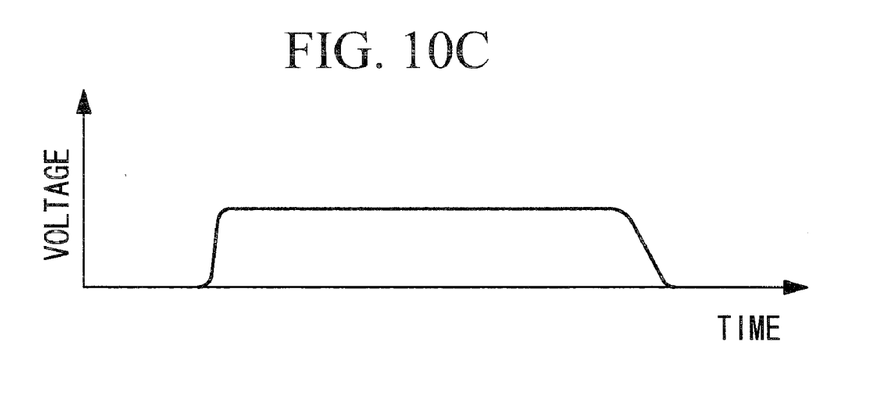

Now, when digital signals are successively input from the control unit 7 to the DA converter 8 at sufficiently short time intervals, successive stimulation pulses are generated, as shown in FIG. 10A. When the pulse time intervals are sufficiently short, the successive stimulation pulses are shaped into a waveform shown in FIG. 10B through the pulse transformer 5 and then input to the smoothing circuit 11. Finally, a stimulation pulse having a substantially uniformly smoothed voltage is supplied to the vagus nerve B, as shown in FIG. 10C. In order that the voltage of the successive stimulation pulses is smoothed sufficiently at this time, as the smoothing circuit 11, a smoothing circuit having suitable specifications, such as the capacitance of the capacitor 11b, is used.

The pulse transformer 5 used here is the same as that used in the first embodiment.

Similarly to the first embodiment, the control unit 7 detects bradycardia, tachycardia, and fibrillation.

Upon detecting tachycardia, the control unit 7 outputs digital signals to the DA converter 8 successively at sufficiently short time intervals. Regarding the successive stimulation pulses generated at this time, for example, assuming that the voltage of the stimulation pulses output from the DA converter 8 is 10 V and the VT product of the pulse transformer 5 is 30 μs·V, the pulse width of each stimulation pulse is set to be 2 μs, and the time interval of stimulation pulses is set to be 0.5 μs. In this case, the pulse width of the stimulation pulse shaped into a single pulse is extended by 2.5 μs each time the number of digital signals successively output by the control unit 7 is increased by one.

The number of digital signals successively output by the control unit 7 is set on the basis of the magnitude of energy that is to be supplied to the vagus nerve B. For example, when the heart treatment device 1 is embedded inside the body of a patient, stimulation pulses are supplied to the vagus nerve B while gradually increasing the number of digital signals, and it is observed whether the vagus nerve B responds. Thus, the minimum number of digital signals with which the vagus nerve B exhibits a response, i.e., the capture threshold of the vagus nerve B, is checked. The minimum number of digital signals ascertained at this time is set as the minimum number of successive stimulation pulses that are to be supplied to the vagus nerve B of the patient. Then, the number of digital signals is set to be not less than the minimum value and within such a range that an excessive load is not imposed on the vagus nerve B.

Furthermore, when the time interval T of heartbeats after the stimulation pulses are supplied does not exceed the first predetermined lower limit T1, so that stimulation pulses are to be supplied again, the control unit 7 compares the time intervals T of heartbeats before and after the last stimulation pulses are supplied. Then, if the time interval T of heartbeats after the stimulation pulses are supplied is longer than that before the stimulation pulses are supplied, the control unit 7 decreases the number of digital signals that are output next. On the other hand, if the time interval T of heartbeats after the stimulation pulses are supplied is the same as or shorter than that before the stimulation pulses are supplied, the control unit 7 increases the number of digital signals that are output next.

Figure 11:
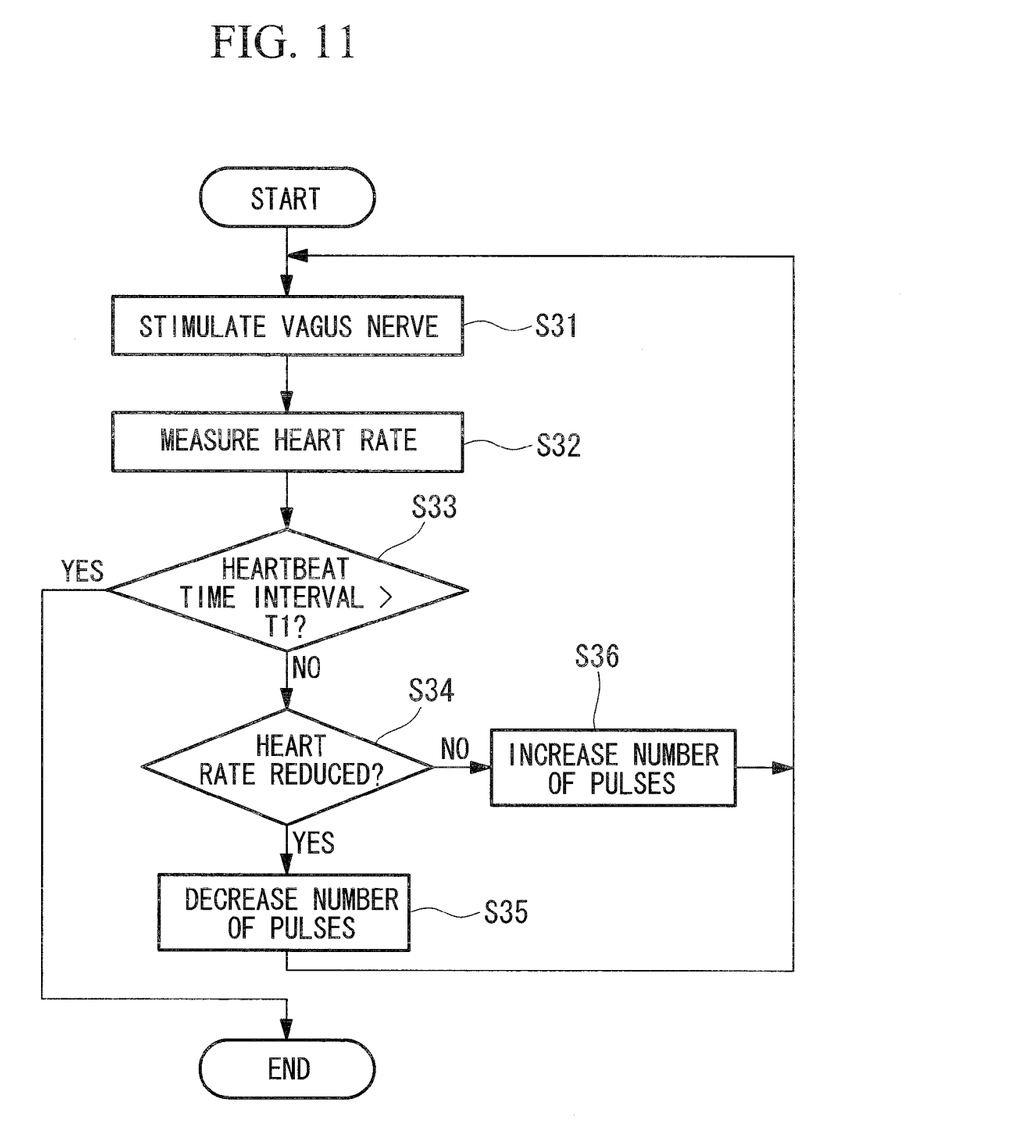
FIG. 11 is a flowchart for explaining an operation for stimulating the vagus nerve with the heart treatment device shown in FIG. 8.

The operation of the thus-configured heart treatment device 1 will be described below with reference to FIG. 11.

Figure 3:
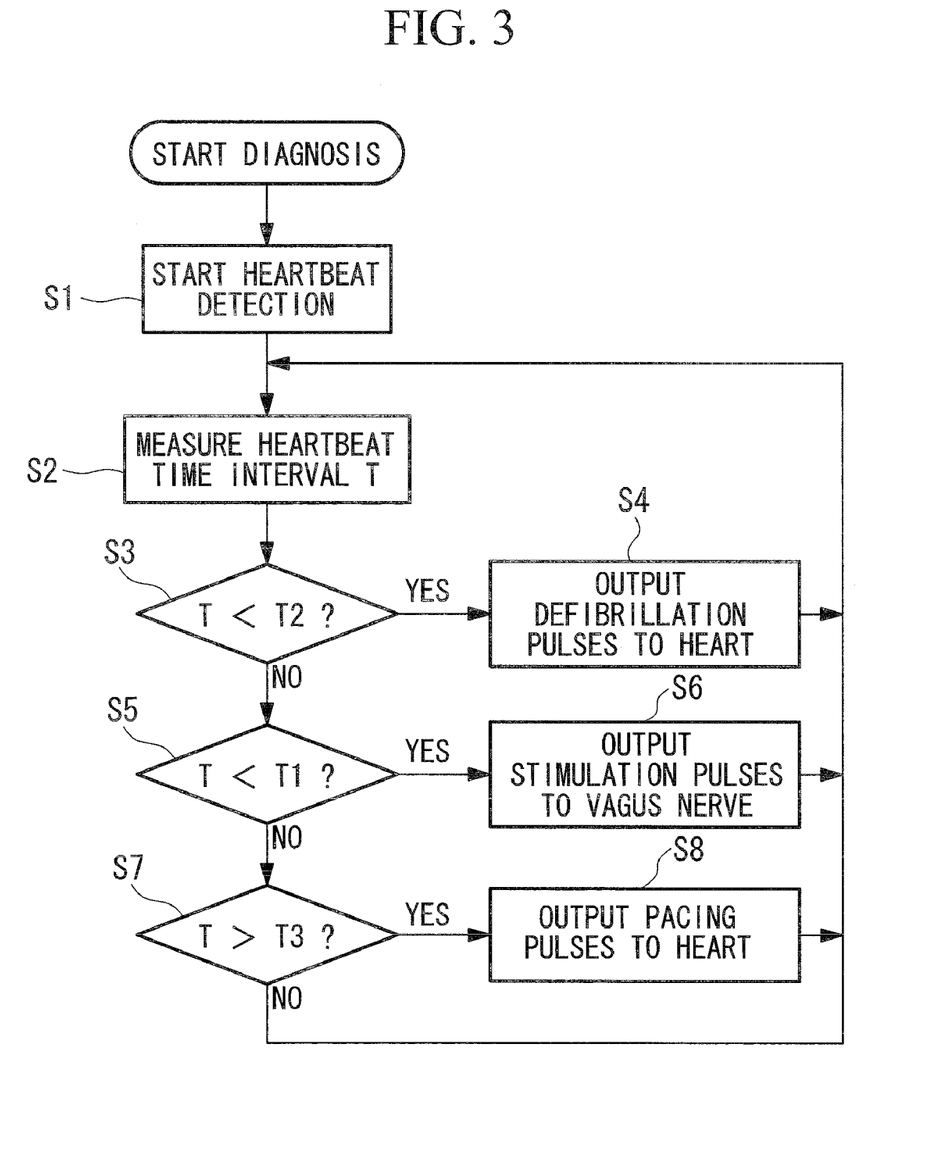
FIG. 3 is a flowchart for explaining the operation of the heart treatment device shown in FIG. 1.

Upon commencing heartbeat detection, similarly to the case of the first embodiment shown in FIG. 3, on the basis of the time interval T of heartbeats, the heart treatment device 1 according to this embodiment supplies defibrillation pulses or pacing pulses to the heart A or supplies stimulation pulses to the vagus nerve B.

When tachycardia of the heart A occurs, the heart treatment device 1 outputs stimulation pulses to the vagus nerve B (step S31), and then determines whether the time interval T of heartbeats measured after the output (step S2) has become longer than the normal value T1 (step S33). If it is determined as a result that the time interval T has become longer than the normal value T1, the heart treatment device 1 continues monitoring the time interval T of heartbeats again (i.e., diagnosis is started according to the flow shown in FIG. 3).

On the other hand, if the time interval T of heartbeats does not become longer than the normal value T1 even when stimulation pulses are supplied, the heart treatment device 1 determines whether the time interval T of heartbeats after the stimulation pulses are supplied has become longer than before (step S34). If it is determined as a result that the time interval T of heartbeats after the stimulation has become longer than before, the number of stimulation pulses is decreased (step S35), and the vagus nerve B is stimulated again (step S31). On the other hand, if the time interval T of heartbeats after the stimulation has not become longer than before, the number of stimulation pulses is increased (step S36), and the vagus nerve B is stimulated again (step S31). Then, the above operation is repeated until the time interval T of heartbeats after stimulating the vagus nerve B becomes longer than the normal value T1.

As described above, according to this embodiment, similarly to the first embodiment, it is possible to prevent leakage of stimulation pulses to the heartbeat detecting circuit 2 and accurately detect heartbeats. Furthermore, an advantage is afforded in that reduction in power consumption and size reduction of the heart treatment device 1 can be achieved. Furthermore, by using a pulse transformer with an even smaller VT product, an advantage is afforded in that the size of the heart treatment device 1 can be reduced further and the intensity of stimulation pulses can be further optimized.

Furthermore, since the sensitivity of the vagus nerve B to electric pulses varies among individuals, it is desired that the magnitude of the energy of electric pulses be set for each patient. However, existing heart treatment devices are not configured to support this feature. Thus, there is a disadvantage that it is not possible to set the specifications of electric pulses optimally for each patient. In contrast, with the heart treatment device 1 according to this embodiment, a single pulse formed of a plurality of stimulation pulses each restricted to a small energy by the pulse transformer 5 is supplied to the vagus nerve B. Thus, the magnitude of the stimulation pulse as a whole supplied to the vagus nerve B can be appropriately and readily adjusted based on a sufficiently small width. Accordingly, it is possible to prevent imposing an excessive load on the vagus nerve B. Furthermore, an advantage is afforded in that it is possible to apply to the vagus nerve B stimulation with an appropriate intensity suitable for treatment of each patient.

Furthermore, when the vagus nerve B is stimulated, in accordance with whether an effect of stimulation pulses is observed, the energy of the stimulation pulses is adjusted. Thus, when an effect of stimulation is observed, stimulation is weakened while being applied to the vagus nerve B, so that the burden on the vagus nerve B can be alleviated further. On the other hand, when an effect of stimulation is not observed, stimulation is intensified gradually while observing whether any effect arises, so that it is possible to prevent excessive stimulation of the vagus nerve B.

Although the time interval T of heartbeats is constantly monitored in the first and second embodiments described above, alternatively, the heart rate may be monitored. The time interval T of heartbeats and the heart rate are in a reciprocal relationship.

The embodiments of the present invention have the following aspects.

The embodiments provide a heart treatment device including a heartbeat detecting unit that detects heartbeats by using an electrode disposed at a heart; a pulse transformer having a primary winding and a secondary winding, the heartbeat detecting unit being disposed on the side of the primary winding, and the secondary winding being connected to the vagus nerve; and a pulse generating unit that supplies an electric pulse to the primary winding of the pulse transformer on the basis of the heartbeats detected by the heartbeat detecting unit, the electric pulse having a pulse width not exceeding the voltage-time product of the pulse transformer.

According to the embodiments, when the heart rate increases and the time interval of heartbeats detected by the heartbeat detecting unit becomes short, an electric pulse is supplied from the pulse generating unit to the vagus nerve via the pulse transformer. Thus, it is possible to reduce and stabilize the heart rate.

In this case, since an electric pulse having a sufficiently short pulse width, restricted by the voltage-time product of the pulse transformer, is supplied to the vagus nerve, it is possible to prevent excessive stimulation of the vagus nerve or unintended effects on the vagus nerve. Furthermore, since the pulse transformer electrically insulates the heartbeat detecting unit and the vagus nerve from each other, leakage to the heartbeat detecting unit of the electric pulse supplied to the vagus nerve is prevented. Thus, it is possible to detect heartbeats accurately even while the vagus nerve is being stimulated. Furthermore, by supplying electric power from the primary winding to the secondary winding of the pulse transformer, it suffices to provide an electric power supply only on the side of the primary winding of the pulse transformer. Accordingly, it is possible to reduce the size and power consumption of the heart treatment device.

In the embodiments, the heart treatment device may further include an electric-power supplying unit that is disposed on the side of the primary winding of the pulse transformer and that supplies electric power to the pulse generating unit, and the winding ratio of the secondary winding relative to the primary winding of the pulse transformer may be greater than the ratio of the voltage of the electric pulse relative to the voltage of the electric power supplied by the electric-power supplying unit.

Accordingly, the electric pulse output from the pulse generating unit is boosted by the pulse transformer from the voltage supplied from the electric-power supplying unit before it is supplied to the vagus nerve. Thus, a component for boosting the voltage of the electric pulse, such as a boosting circuit, becomes unnecessary. This serves to further reduce the size and power consumption of the heart treatment device.

Furthermore, in the embodiments, the heart treatment device may include a plurality of pulse transformers, the pulse generating unit may generate electric pulses successively, and the heart treatment device may further include rectifying circuits that limit currents flowing from the vague nerve to the individual pulse transformers, the rectifying circuits being disposed between the individual pulse transformers and the vagus nerve; and transformer selecting means for selecting a pulse transformer to which the electric pulse is supplied by the pulse generating unit so that the successive electric pulses are supplied to different pulse transformers.

Accordingly, electric pulses are supplied to the vagus nerve successively from the plurality of pulse transformers. Thus, even if the pulse width of each electric pulse is too short to stimulate the vagus nerve sufficiently, it is possible to provide a sufficiently long pulse width as a whole electric pulse supplied to the vagus nerve. Furthermore, the rectifying circuits serve to prevent an unintended pulse transformer from acting as a load. Furthermore, an electric pulse supplied from one pulse transformer to the vagus nerve is prevented from flowing into another pulse transformer via the vagus nerve. Thus, it is possible to prevent leakage of an electric pulse to the heartbeat detecting circuit more reliably.

Furthermore, in the above configuration, the pulse generating unit may be configured to generate electric pulses having different voltages.

Accordingly, by combining electric pulses having different voltages, it becomes possible to shape a whole electric pulse supplied to the vagus nerve more suitably for stimulation of the vagus nerve. This serves to improve the effectiveness of the treatment.

In the embodiments, the pulse generating unit may supply electric pulses successively at time intervals, and the heart treatment device may further include a nerve connecting unit connected to the vagus nerve; a control unit that controls the number of the successive electric pulses supplied by the pulse generating unit to the primary winding of the pulse transformer; and smoothing means for smoothing the voltage of the successive electric pulses conveyed from the secondary winding of the pulse transformer, the smoothing means being connected between the secondary winding and the nerve connecting unit.

Accordingly, individual electric pulses output from the pulse generating unit have a sufficiently small energy, restricted by the voltage-time product of the pulse transformer, and the electric pulses are smoothed by the smoothing means and supplied to the vagus nerve in an integrated form. That is, it is possible to readily adjust the magnitude of the energy of a whole electric pulse supplied to the vagus nerve merely by increasing or decreasing the number of electric pulses supplied to the pulse transformer under the control of the control unit. Thus, it is possible to apply stimulation of a suitable intensity needed for treatment to the vagus nerve. Furthermore, since a small voltage-time product of the pulse transformer suffices, by using a pulse transformer of an even smaller size, it is possible to further reduce the size of the heart treatment device.

Furthermore, in the above configuration, the control unit may be configured to control, after the successive electric pulses are supplied to the primary winding of the pulse transformer, the number of successive electric pulses in accordance with change in the heartbeats detected by the heartbeat detecting unit.

Accordingly, stimulation is applied to the vagus nerve while being adjusted to be more intense or weaker in accordance with whether an effect of treatment is observed. Thus, it is possible to further reduce the load of the vagus nerve and improve the effectiveness of the treatment.

According to the embodiments, an advantage is afforded in that it is possible to prevent excessive stimulation of the vagus nerve or unintended effects on the vagus nerve due to stimulation and to reduce size and power consumption while maintaining the accuracy of heartbeat detection.

Furthermore, according to the embodiments, an advantage is afforded in that it is possible to apply stimulation of an appropriate intensity to the vagus nerve while maintaining the accuracy of heartbeat detection and reducing size and power consumption.

What is claimed is:

1. A heart treatment device comprising:
   a heartbeat detecting unit that detects heartbeats by using an electrode disposed at a heart;
   a pulse transformer having a primary winding and a secondary winding, the heartbeat detecting unit being disposed on the side of the primary winding, and the secondary winding being connected to the vagus nerve; and
   a pulse generating unit that supplies an electric pulse to the primary winding of the pulse transformer on the basis of the heartbeats detected by the heartbeat detecting unit, the electric pulse having a pulse width not exceeding the voltage-time product of the pulse transformer.

2. A heart treatment device according to claim 1, further comprising an electric-power supplying unit that is disposed on the side of the primary winding of the pulse transformer and that supplies electric power to the pulse generating unit,
   wherein the winding ratio of the secondary winding relative to the primary winding of the pulse transformer is greater than the ratio of the voltage of the electric pulse relative to the voltage of the electric power supplied by the electric-power supplying unit.

3. A heart treatment device according to claim 1, comprising a plurality of pulse transformers,
   wherein the pulse generating unit generates electric pulses successively, and
   wherein the heart treatment device further comprises:
   rectifying circuits that limit currents flowing from the vagus nerve to the individual pulse transformers, the rectifying circuits being disposed between the individual pulse transformers and the vagus nerve; and
   transformer selecting means for selecting a pulse transformer to which the electric pulse is supplied by the pulse generating unit so that the successive electric pulses are supplied to different pulse transformers.

4. A heart treatment device according to claim 3, wherein the pulse generating unit generates electric pulses having different voltages.

5. A heart treatment device according to claim 1,
   wherein the pulse generating unit supplies electric pulses successively at time intervals, and
   wherein the heart treatment device further comprises:
   a nerve connecting unit connected to the vagus nerve;
   a control unit that controls the number of the successive electric pulses supplied by the pulse generating unit to the primary winding of the pulse transformer; and
   smoothing means for smoothing the voltage of the successive electric pulses conveyed from the secondary winding of the pulse transformer, the smoothing means being connected between the secondary winding and the nerve connecting unit.

6. A heart treatment device according to claim 5, wherein, after the successive electric pulses are supplied to the primary winding of the pulse transformer, the control unit controls the number of successive electric pulses in accordance with a change in the heartbeats detected by the heartbeat detecting unit.

* * * * *